United States Patent [19]

Rao

[11] Patent Number: 5,246,927
[45] Date of Patent: Sep. 21, 1993

[54] BENZAZOLE DERIVATIVES, PROCESSES FOR THEIR PREPARATION CONTAINING SUCH COMPOUNDS AND THE USE THEREOF

[75] Inventor: Vittal R. Rao, Bombay, India
[73] Assignee: Ciba-Geigy Corporation, Ardsley, N.Y.
[21] Appl. No.: 957,641
[22] Filed: Oct. 6, 1992

Related U.S. Application Data

[63] Continuation of Ser. No. 754,337, Sep. 4, 1991, abandoned, which is a continuation-in-part of Ser. No. 501,705, Mar. 29, 1990, abandoned, which is a continuation-in-part of Ser. No. 388,775, Aug. 2, 1989, abandoned.

[30] Foreign Application Priority Data

Aug. 17, 1988 [GB] United Kingdom ............... 8819545

[51] Int. Cl.$^5$ ............... C07D 263/54; C07D 277/64; A61K 31/495; A61K 31/42
[52] U.S. Cl. .............................. 514/212; 514/228.2; 514/233.8; 514/252; 514/255; 514/321; 514/367; 514/369; 514/375; 540/480; 540/603; 544/58.7; 544/135; 544/369; 546/198; 548/178; 548/188; 548/217
[58] Field of Search ............... 514/212, 255, 228.2, 514/233.8, 252, 321, 367, 875, 369; 540/480, 603; 544/58.7, 135, 369; 546/198; 548/178, 188, 217

[56] References Cited

U.S. PATENT DOCUMENTS

| | | | |
|---|---|---|---|
| 3,934,017 | 1/1976 | Gallay et al. | 514/321 |
| 4,511,567 | 4/1985 | Galley et al. | 548/178 |
| 4,649,149 | 5/1987 | Galley | 514/367 |
| 4,680,301 | 7/1987 | Rao | 546/198 |

FOREIGN PATENT DOCUMENTS

| | | | |
|---|---|---|---|
| 175650 | 5/1986 | European Pat. Off. | 546/198 |
| 356385 | 2/1990 | European Pat. Off. | 514/255 |
| 2076399 | 9/1981 | United Kingdom | 514/367 |

OTHER PUBLICATIONS

J. Med Chem 25:8 969 (1982).

Primary Examiner—Mukund J. Shah
Assistant Examiner—E. C. Ward
Attorney, Agent, or Firm—Irving M. Fishman; Karen G. Kaiser

[57] ABSTRACT

The invention relates to new benzazole derivatives of the formula I

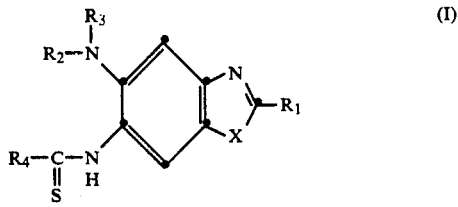

wherein X is oxygen or sulphur, $R_1$ is lower alkyl, lower alkenyl or cycloalkyl, $R_2$ and $R_3$ independently of one another are each hydrogen, lower alkyl or cycloalkyl radicals or taken together are a substituted or unsubstituted bivalent hydrocarbon residue of aliphatic character in which the carbon atoms of the chain may be interrupted by a heteroatom, $R_4$ is either a group

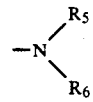

wherein $R_5$ and $R_6$ independently of one another are lower alkyl or cycloalkyl radicals, optionally substituted, or taken together $R_5$ and $R_6$ are a substituted or unsubstituted bivalent hydrocarbon residue of aliphatic character in which the carbon atoms of the chain may be interrupted by a heteroatom, or, $R_4$ is a group

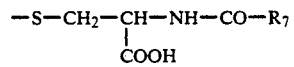

where $R_7$ is a lower alkyl group, and their salts and N-oxides. The products are useful as anthelmintic effective agents. The products can be prepared to methods known per se.

20 Claims, No Drawings

BENZAZOLE DERIVATIVES, PROCESSES FOR THEIR PREPARATION CONTAINING SUCH COMPOUNDS AND THE USE THEREOF

This application is a continuation of application Ser. No. 754,337, filed Sep. 4, 1991, abandoned which is a Continuation-in-part of 07/501,705 Mar. 29, 1990, abandoned which is a Continuation-in-part of 07/388,775 Aug. 2, 1989, abandoned The invention relates to new benzazole derivatives of the formula I

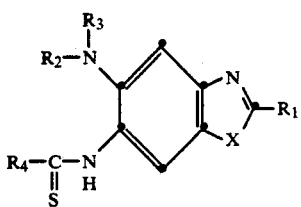

wherein X is oxygen or sulphur, $R_1$ is lower alkyl, lower alkenyl or cycloalkyl, $R_2$ and $R_3$ independently of one another are each hydrogen, lower alkyl or cycloalkyl radicals or taken together are a substituted or unsubstituted bivalent hydrocarbon residue of aliphatic character in which the carbon atoms of the chain may be interrupted by a heteroatom, $R_4$ is either a group

wherein $R_5$ and $R_6$ independently of one another are lower alkyl or cycloalkyl radicals, optionally substituted, or taken together $R_5$ and $R_6$ are a substituted or unsubstituted bivalent hydrocarbon residue of aliphatic character in which the carbon atoms of the chain may be interrupted by a heteroatom, or, $R_4$ is a group

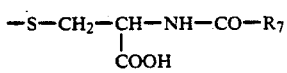

where $R_7$ is a lower alkyl group, and their salts and N-oxides and processes for their preparation, pharmaceutical preparations containing them and their uses.

The term 'lower' used to qualify radicals denotes that these contain up to 7 carbon atoms, preferably up to 4 carbon atoms.

Lower alkyl and alkenyl radicals may be straight-chain or branched-chain radicals substituted by free, esterified or etherified hydroxy groups such as lower alkanoyloxy, lower alkoxy or lower alkenyloxy groups, free or esterified carboxyl groups such as lower alkoxy-carbonyl, as for example, methoxy or ethoxy-carbonyl, dialkylamino, lower alkyl thio and lower alkenyl thio or halogen atoms.

Halogen atoms are in particular fluorine, chlorine or bromine atoms but can also be iodine atoms.

Lower alkyl groups are, for example, preferably methyl groups and also ethyl, n-propyl, isopropyl, n-butyl, isobutyl, sec-butyl, tert-butyl. Lower alkenyl groups are, for example, the allyl group or 2-methylallyl group. Substituted lower alkyl groups are, for example, the trifluoromethyl group or a free or esterified carboxymethyl group, for example, the methoxycarbonylmethyl group.

A cycloalkyl group is primarily a monocyclic residue having, for example, 3 to 10 carbon atoms, preferably 5 to 7 carbon atoms, for example, a cyclopentyl, cyclohexyl and cycloheptyl group.

The groups $R_2$ and $R_3$ or $R_5$ and $R_6$ when taken together represent an optionally substituted bivalent hydrocarbon residue of aliphatic character which contains between 4 and 7 carbon atoms in the chain. The substituents on the bivalent hydrocarbon may be one or more lower alkyl groups or an optionally substituted phenyl radical. Thus the substituted bivalent hydrocarbon radical, e.g. as lower alkylene together with the nitrogen atom represents a heterocyclic radical such as pyrrolidino, piperidino, 4-methyl or 4-phenyl piperidino, hexahydroazepino or octahydroazocino group. The bivalent hydrocarbon chain may be interrupted by a hetero atom, for example, oxygen, sulphur, substituted or unsubstituted nitrogen representing as oxa-lower alkyleneamino, for example, morpholino, 2,6-dimethylmorpholino, or as thia-lower alkyleneamino, for example, thiamorpholino, or optionally substituted aza-lower alkyleneamino, for example, N-methyl, N-phenyl, N-acetyl, N-methoxycarbonyl, N-ethoxycarbonyl- or N-methanesulphonyl piperazino groups as well as their N-oxides. Substituents on the optionally substituted nitrogen atom which interrupt the bivalent hydrocarbon chain as indicated above may be an optionally substituted lower alkyl group or an aryl group such as phenyl groups, an acyl group such as lower alkanoyl, e.g. acetyl, or aroyl, e.g. benzoyl, or a lower alkoxycarbonyl group such as ethoxycarbonyl or methoxycarbonyl or an alkanesulphonyl group such as methanesulphonyl.

The benzene nucleus may be optionally substituted by lower alkyl, alkoxy, carbalkoxy groups or halogen atoms.

The novel compounds have valuable pharmacological properties. They are useful in the control of parasitic helminths such as nematodes, cestodes and trematodes. They are particularly useful in the control of pathogens in filariasis such as *Litomosoides carinii, Brugia malayi, Brugia pahangi* and *Dipetalonema viteae* and of their developmental stages. In the treatment of filariasis in multimammate rat (*Mastomys natalensis*) and birds (*Meriones unguiculatus*), the new compounds have proved to be very potent as macro and microfilaricides on administration orally 1–5 times of dose of 6.25 to 25 mg/kg.

Thus, the present invention is additionally directed to a method for the treatment of lymphatic and tissue-dwelling filarial infections in an animal in need of such treatment which comprises the administration to said animal of an antifilarially effective amount of a compound according to the present invention or a pharmaceutically acceptable salt thereof and a method for the treatment of intestinal helminthic infections in an animal in need of such treatment which comprises the administration to said animal of an antihelminthically effective amount of a compound according to the present invention or a pharmaceutically acceptable salt thereof. The compound 2-tert-butyl-6-[(4-methylpiperazin-1-yl)-thiocarbonylamino]-5-(4-methylpiperidin-1-yl)-benzothiazole has been found to have high activity against Brugia malayi in leaf monkeys. The compound is curative (fully effective) against microfilariae and adult worm at a single dose of 50 mg/kg as well as at a dose of 25 mg/kg given consecutively on 5 days.

It has been found that compounds according to Rao (U.S. Pat. No. 4,680,301) in which the grouping

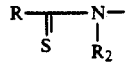

is different from an isothiocyanato group very easily reverts to compounds in which said grouping

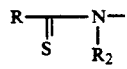

is an isothiocyanate ($R_2$ and $R_3$ being an additional bond). The compounds according to the present invention are stable and do not revert to the isothiocyanate and hence do not react with endogenous proteins at blood pH. The free isothiocyanates according to Rao react under these conditions, leading to erratic and poor absorptions. Compounds according to the present invention are taken up by fat tissues and release at a slow rate. The fat acts as a depot for slow release. This results in lower blood levels and lower CNS related side effects. The parasites live in lymph nodes in lymphatic filariasis and hence the lipophilicity of the compounds of this invention coupled with the described slow release would be an advantage in the treatment of this disease.

Particularly useful by virtue of their potent antifilarial activity are compounds of the formula I wherein X is sulphur or oxygen, $R_1$ is lower alkyl, and $R_2$ and $R_3$ together represent lower alkylene optionally interrupted by oxygen, sulphur or nitrogen with a total of 4 to 6 carbon atoms wherein nitrogen is optionally substituted by lower alkyl, lower alkanoyl or lower alkoxycarbonyl group and $R_4$ is a group

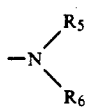

wherein $R_5$ and $R_6$ taken together are lower alkylene optionally interrupted by oxygen or optionally substituted nitrogen with a total of 4 to 6 carbon atoms, $R_4$ e.g. thus constituting a heterocyclic group such as pyrrolidino, piperidino, hexahydroazepino, morpholino, piperazino, 4-methyl piperazino and its N-oxide, 4-acetylpiperazino, 4-carbethoxypiperazino groups, or, $R_4$ is a group

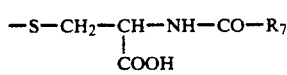

where $R_7$ is a lower alkyl group.

Of particular interest are compounds of the formula I, wherein X is sulphur, $R_1$ is lower alkyl with 3 and 4 carbon atoms, and $R_2$ and $R_3$ together represent lower alkylene with a total of 4 to 6 carbon atoms in the chain optionally interrupted by oxygen or nitrogen wherein nitrogen is optionally substituted by lower alkyl or lower alkoxy carbonyl, and $R_4$ is a group

where $R_5$ and $R_6$ together are lower alkylene with a total of 4 to 6 carbon atoms in the chain optionally interrupted by oxygen or nitrogen wherein nitrogen is optionally substituted by lower alkyl, lower alkanoyl or lower alkoxycarbonyl, $R_4$ thus constituting e.g. a heterocyclic group such as a piperidino group, piperazino group and 4-methylpiperazino group and its N-oxide thereof or $R_4$ is a group

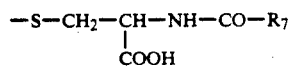

where $R_7$ is a lower alkyl group, e.g. methyl.

The most preferred compounds of formula I are compounds, wherein X is sulphur, $R_1$ is tert-butyl, $R_2$ and $R_3$ together with the nitrogen atom form a heterocyclic group, such as piperidino optionally substituted by lower alkyl group, $R_4$ is a group $—N(R_5R_6)$ wherein $R_5$ and $R_6$ together with the nitrogen atom form a heterocyclic group, such as piperidino or piperazino with a lower alkyl, alkanoyl or alkoxycarbonyl group as substituent on the nitrogen atom of the piperazine, or $R_4$ is $—S—CH_2—CH(COOH)—NH—CO—R_7$ wherein $R_7$ is a methyl group, and their pharmaceutically acceptable salts.

The invention relates especially to compounds of the formula I mentioned in the Examples and their salts. Particularly mentioned are the following compounds:
2-Tert-butyl-6-[(4-methylpiperazin-1-yl)thiocarbonylamino]-5-(4-methylpiperidin-1-yl)benzothiazole.
2-Tert-butyl-6-[4-methylpiperazin-1-yl)thiocarbonylamino]-5-(piperidin-1-yl)benzothiazole.
2-Tert-butyl-5-(piperidin-1-yl)-6-[(piperidin-1-yl)thiocarbonylamino]benzothiazole.
2-Tert-butyl-6-[(morpholin-4-yl)thiocarbonylamino]-5-(piperidin-1-yl)benzothiazole.
2-Tert-butyl-6-[(piperidin-1-yl)thiocarbonylamino]-5-(4-methylpiperazin-1-yl)benzothiazole.
S-(Acetamido-2-carboxyethyl)-N-[2-tert-butyl-5-(4-methylpiperidin-1-yl)benzothiazol-6-yl]dithiocarbamate.
S-(Acetamido-2-carboxyethyl)-N-[2-tert-butyl-5-(piperidin-1-yl)benzothiazol-6-yl]dithiocarbamate.

According to the present invention there is provided a process for the preparation of novel benzazole derivatives of the formula I, wherein X, $R_1$, $R_2$, $R_3$ and $R_4$ have the meanings defined above, which comprises the reaction of an isothiocyanatobenzazole of the formula II

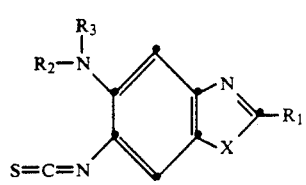

wherein X, $R_1$, $R_2$ and $R_3$ have the meanings defined above, with a nucleophilic compound of the formula R4—H. The nucleophile R4—H can have either the formula III

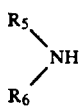

wherein $R_5$ and $R_6$ independently of one another are lower alkyl or cycloalkyl radicals, optionally substituted, or taken together $R_5$ and $R_6$ are a substituted or unsubstituted bivalent hydrocarbon residue of aliphatic character in which the carbon atoms of the chain may be interrupted by a heteroatom, or, R4—H can have the formula IV

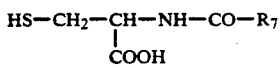

where $R_7$ is a lower alkyl group.

Starting compounds of the formula II can be prepared by methods described in European Patent Application No. 85810418.5 published under No. 0175650 from the corresponding 6-amino benzazoles. The preferred procedures for this conversion are the reaction of the amines with ammonium thiocyanate to yield the thioureas and pyrolysis of the latter to yield the isothiocyanates or the direct conversion of the amines by treatment with thiophosgene to yield the isothiocyanates.

The reaction of the isothiocyanates II with the nucleophile R4—H can be carried out in solvents such as chloroform, methylene dichloride, ethanol or dimethyl formamide.

The process described can be carried out in the conventional manner at ambient temperature, with cooling or warming, under normal pressure or elevated pressure and, if necessary, in the presence or absence of a diluent, catalyst or condensing agent. If necessary, the reaction can also be carried out in the atmosphere of an inert gas, for example, nitrogen.

In resulting compounds substituents can be introduced, modified or detached within the scope of the definition of the end products.

Compounds of the formula I wherein

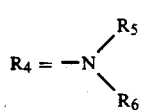

can also be obtained by the reaction of 6-aminobenzazoles of the formula V

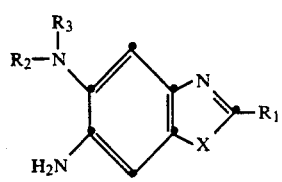

with a thiocarbamoyl halide of formula VI

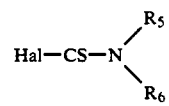

in which Hal is chlorine or bromine in the presence of an acid binding agent.

Another method of obtaining compounds of the formula I wherein

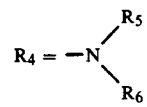

is to react a thiocarbamic acid derivative of formula VII,

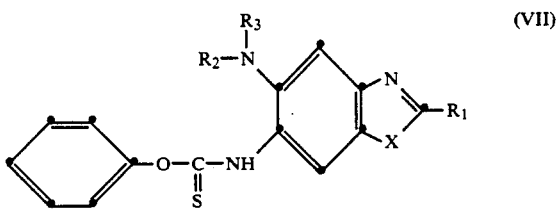

wherein X, $R_1$, $R_2$, and $R_3$ have the meanings as defined above under formula I, with an amine of the formula III

Compounds of formula VII are obtained by reacting a 6-aminobenzazole of formula V with a halothiocarboxylic acid-O-phenyl ester or O,O-diphenyl thiocarbonate.

The invention also relates to these embodiments of a process in which a process is discontinued at any stage or in which a compound obtainable as an intermediate at any stage is used as a starting material and the missing process steps are carried out, or a starting material is formed under the reaction conditions, or if desired, is used in the form of a salt. The invention also includes novel intermediates resulting therefrom.

Depending on the process conditions and the starting materials the end products are obtained in the free form or in the form of their salts, especially acid addition salts which are also included in the invention. The acid addition salts of the novel compounds can be converted to the free compound in a manner known per se, for example with basic agents such as alkali or ion exchangers. On the other hand the resulting free bases can form salts with organic or inorganic acids. Acids used to prepare acid addition salts are in particular those which are suitable for forming therapeutically usable salts.

The following may be mentioned as examples of suitable acids: hydrohalic acids, sulfuric acids, phosphoric acids, nitric acid, perchloric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid or pyruvic acid; phenylacetic acid, benzoic acid, p-aminobenzoic acid, anthranilic acid, p-hydroxybenzoic acid, salicylic acid or p-aminosalicyclic acid, embonic acid, methane-sulfonic acid, ethanesulfonic acid, hydroxyethanesulfonic acid, or ethylenesulfonic acid; halogenobenzenesulfonic acid, toluenesulfonic acid, naphthalenesulfonic acid or sulfanilic acid; and methionine, tryptophane, lysine or arginine.

Evaluation in the animal test systems mentioned above show the excellent potential of the novel compounds as micro and macrofilaricides, for example, for lymphatic filariasis and onchocerciasis for which an effective dosage range of 6.25 to 50 mg/kg daily by oral administration over a period of one to 5 days is to be used. The compounds may be used for the treatment of lymphatic and tissue-dwelling filarial infections in animals including man. The compounds may also be used for the treatment of intestinal helminthic infections like ancylostomiasis, ascariasis, oxyuriasis and trichuriasis and also schistosomiasis in animals and in human beings at dose range of 10 to 500 mg/kg.

The pharmaceutical preparations according to the invention, which contain compounds of the formula I or pharmaceutically acceptable salts thereof, are those for enteral, such as oral or rectal, and parenteral, administration to warm-blooded animals, that contain the pharmacologically active substance alone or together with a pharmacologically acceptable carrier. The dosage of the active substance depends on the species of warm-blooded animal, the age and the individual condition, and on the method of administration.

The new pharmaceutical preparations contain, for example, from approximately 10% to approximately 80% preferably from approximately 20% to approximately 60% of the active substance. Pharmaceutical preparations according to the invention for enteral or parenteral administration are, for example, those in dosage unit forms, such as dragess, tablets, capsules, suppositories, or also ampoules. These are produced in a manner known per se, for example by means of conventional mixing, granulating, coating, dissolving or lyophilising processes. Thus, pharmaceutical preparations for oral administration can be obtained by combining the active substance with solid carriers, optionally granulating a resulting mixture, and processing the mixture or granulate to form tablets or dragee cores, if desired or necessary after the addition of suitable adjuncts.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatin, tragacanth, methylcellulose and/or polyvinylpyrrolidone, and/or if desired, disintegrators, such as the above-mentioned starches, and also carboxymethylstarch, cross-linked polyvinylpyrrolidone, agar, alginic acid or a salt thereof, such as sodium alignate. Adjuncts are especially flow-regulating agents and lubricants, for example, silica, talc, stearic acid or salts thereof, such as magnesium or calcium stearate, and/or polyethylene glycol. Dragee cores are provided with suitable, optionally gastric juice-resistant coating, there being used, inter alia, concentrated sugar solutions, which optionally contain gum arabic, talc, polyvinylpyrrolidone, polyethylene glycol and/or titanium dioxide, lacquer solutions in suitable organic solvents or solvent mixtures or, to produce gastric juice-resistant coating, solutions of suitable cellulose preparations, such as acetylcellulose phthalate or hydroxypropylmethylcellulose phthalate. Colouring matter or pigments may be added to the tablets or dragee coating, for example for identification purposes or for indicating different doses of active substance.

Other pharmaceutical preparations for oral administration are dry-filled capsules made of gelatin, and soft sealed capsules consisting of gelatin and a plasticiser, such as glycerin or sorbitol. The dry-filled capsules may contain the active substance in the form of a granulate, for example, in admixture with fillers, such as lactose, binders, such as starches, and/or glidants, such as talc or mangesium stearate, and optionally, stabilisiers. In soft capsules the active substance is preferably dissolved or suspended in suitable liquids, such as fatty oils, paraffin oil or liquid polyethylene glycols, it likewise being possible for stabilisers to be added.

These come into consideration as rectally administerable pharmaceutical preparations, for example, suppositories consisting of a combination of the active substance with a suppository base. Suitable suppository bases are, for example, natural or synthetic triglycerides, paraffin hydrocarbons, polyethylene glycols or higher alkanols. It is also possible to use gelatin rectal capsules that contain combination of the active substance with base substances, for example, liquid triglycerides, polyethylene glycols or paraffin hydrocarbons.

Especially suitable forms for parenteral administration are aqueous solutions of an active substance in water-soluble form, for example, a water-soluble salt, or suspensions of the active substance, such as corresponding oily injection suspensions, suitable lipophilic solvents or vehicles, such as fatty oils, for example sesame oil, or synthetic fatty acid esters, for example ethyl oleate or triglycerides, being used, or aqueous injection suspensions that contain viscosity-increasing substances, for example, sodium carboxymethylcellulose, sorbitol and/or dextran and optionally also stabilisers.

Tinctures and solutions usually have an aqueous ethanolic base, to which there are added, inter alia, polyalcohols, for example, glycerin, glycol and/or polyethylene glycol, as moisture-retaining agents for reducing evaporation, and fat-restoring substances, such as fatty acid esters with low polyethylene glycols, that is to say lipophilic substances soluble in aqueous mixture as a replacement for the fatty substances removed from the skin by the alcohol, if necessary, other adjuncts and additives.

The present invention relates also to the use of the compounds of the formula I and the salts of such compounds with salt-forming properties, preferably for combating parasitising helminths, especially those of the families mentioned above.

The following Examples illustrate the above-described invention but are in no way intended to limit the scope thereof. In the following Examples temperatures are in degrees centigrade.

EXAMPLE 1

To a stirred solution of 90 g of 2-tert-butyl-6-isothiocyanato-5-(4-methylpiperidin-1-yl)benzothiazole in 900 ml of methylene chloride is added dropwise 26 g of N-methylpiperazine. The solution is stirred for 1 hour, washed with water, dried over anhydrous sodium sulphate and evaporated to give 110 g of 2-tert-butyl-6-[(4- methylpiperazin-1-yl)thiocarbonylamino]-5-(4-methyl-piperidin-1-yl)benzothiazole, melting at 192°-195° C.

The starting material for the above synthesis is prepared as follows:

A solution of 32,4 g of 2-tert-butyl-5-chloro-6-nitrobenzothiazole, (described in European patent application 85810418.5 published under No. 0175650) in 300 ml of dimethylsulphoxide, is stirred and heated at 140° for 6 hours with 12.8 g of 4-methylpiperidine and 35.8 g of anhydrous potassium carbonate, cooled and poured into water. The solid obtained is dissolved in chloroform and filtered through a silical gel column. The filtate is evaporated to give 2-tert-butyl-5-(4-methylpiperidin-1-yl)-6-nitrobenzothiazole melting at 116°-120°.

A solution of 15.2 g of 2-tert-butyl-5-(4-methyl-piperidin-1-yl)-6-nitrobenzothiazole in 600 ml of methanol is hydrogenated in presence of 6.5 g of Raney Nickel at room temperature. After removing the catalyst the solution is concentrated and the solid filtered to give 6-amino-2-tert-butyl-5-(4-methylpiperidin-1-yl)benzothiazole melting at 146°-148°.

To a cooled mixture of 2.1 g of 6-amino-2-tert-butyl-5-(4-methylpiperidin-1-yl)benzothiazole and 2.8 g of potassium bicarbonate in 20 ml of chloroform is added dropwise 1.6 g of thiophosgene in 5 ml of chloroform under stirring. The stirring is continued for 2 hours maintaining the temperature at 0°-2° . The solid is filtered and the filtrate is evaporated. The solid thus obtained is dissolved in chloroform and filtered through a silica gel column. The filtrate is evaporated to give 2-tert-butyl-6-isothiocyanato-5-(4-methylpiperidin-1-yl)benzothiazole, melting at 54°-58°.

EXAMPLE 2

Using the procedure described in Example 1 by reaction of 2-tert-butyl-6-isothiocyanato-5-(4-methyl-piperazin-1-yl)benzothiazole with 4-methylpiperazine is obtained 2-tert-butyl-6[(4-methylpiperazin-1-yl)thiocarbonylamino]-5-(4-methyl-piperazin-1-yl)benzothiazole, melting at 190°-193°.

The starting material for the above synthesis is prepared as follows:

A solution of 171 g of N-tert-butylthiocarbonyl-2,5-dichloro-4-nitroaniline (described in European patent application No. 85810418.5 published under No. 0175650) and 605 ml of N-methylpiperazine in 1700 ml of dimethylsulphoxide is heated at 140° for 8 hours, cooled and poured into water. The solid is filtered, washed with water and cold isopropanol to yield 2-tert-butyl-5-(4-methylpiperazin-1-yl)-6-nitrobenzothiazole, melting at 132°-135°.

A solution of 86 g of the above nitro compound in 150 ml of ethanol is hydrogenated in presence of 30 g of Raney nickel at 45°. The solution is filtered to give 6-amino-2-tert-butyl-5-(4-methylpiperazin-1-yl)benzothiazole, melting at 130° C.

To a stirred mixture of 75 g of 6-Amino-2-tert-butyl-5-(4-methylpiperazin-1-yl)benzothiazole and 29 g of sodium bicarbonate in 1100 ml of chloroform at 0° is added 41 g of thiophosgene and the mixture stirred at 10° for 4 hours. After filtering off the solid, the solution is evaporated to get a yellow solid which is dissolved in water and the pH of the solution is brought to 7 by the addition of dilute sodium hydroxide. The solid separated is extracted with hexane and filtered through 150 g of neutral alumina to give 2-tert-butyl-6-isothiocyanato-5-(4-methyl-piperazin-1-yl)benzothiazole, melting at 124°-126°.

EXAMPLE 3

Reaction of 2-tert-butyl-6-isothiocyanato-5-(4-methyl-piperazin-1-yl)benzothiazole described in Example 2 with piperidine under conditions described in Example 1 gives 2-tert-butyl-6-[(piperidin-1-yl)thiocarbonylamino]-5-(4-methyl-piperazin-1-yl)benzothiazole, melting at 202°-206°.

EXAMPLE 4

The following compounds can be prepared by the process described in Example 1 by reaction of 2-tert-butyl-6-isothiocyanato-5-(piperidin-1-yl)benzothiazole (described in European Patent application No. 85810418.5) with the appropriate amine:

2-tert-butyl-5-(piperidin-1-yl)-6-[(piperidin-1-yl)thiocarbonylamino]benzothiazole, melting at 183°-186°;

2-tert-butyl-6-[(4-methylpiperazin-1-yl)thiocarbonylamino]-5-(piperidin-1-yl)benzothiazole, melting at 191°-193°;

2-tert-butyl-6-[(4-carbethoxypiperazin-1-yl)thiocarbonylamino]-5-(piperidin-1-yl)benzothiazole, melting at 191°-194°;

2-tert-butyl-6-[(morpholin-4-yl)thiocarbonylamino]-5-(piperidin-1-yl)benzothiazole, melting at 187°-191°;

2-tert-butyl-6-[(hexamethyleneimin-1-yl)thiocarbonylamino]-5-(piperidin-1-yl)benzothiazole, melting at 185°-188°;

N-[2-tert-butyl-5-(piperidin-1-yl)benzothiazol-6-yl]-N'-(2-dimethylaminoethyl)thiourea, melting at 61°-65°;

N-[2-tert-butyl-5-(piperidin-1-yl)benzothiazol-6-yl]-N'-(2-diethylaminoethyl)thiourea, melting at 102°-104°;

N-[2-tert-butyl-5-(piperidin-1-yl)benzothiazol-6-yl]-N'-[3-(piperidin-1-yl)propyl]thiourea, melting at 113°-115°;

N-[2-tert-butyl-5-(piperidin-1-yl)benzothiazol-6-yl]-N'-[3-(4-methylpiperazin-1-yl)propyl]thiourea, melting at 133°-135°;

N-[2-tert-butyl-5-(piperidin-1-yl)benzothiazol-6-yl]-N'-[3-(N,N-dimethylamino)propyl]thiourea, melting at 155°-157°;

N-[2-tert-butyl-5-(piperidin-1-yl)benzothiazol-6-yl]-N'-(2-hydroxyethyl)thiourea, melting at 177°-178°;

2-tert-butyl-6-[(4-methylpiperidin-1-yl)thiocarbonylamino]-5-(piperidin-1-yl)benzothiazole, melting at 214°-217°;

L-N-[2-tert-butyl-5-(piperidin-1-yl)benzothiazol-6-yl]amino-thiocarbonylproline, melting at 183°-187°;

L-$N^\delta$-[2-tert-butyl-5-(piperidin-1-yl)benzothiazol-6-yl)]aminothiocarbonylarginine, melting at 175°-178°;

EXAMPLE 5

A solution of 3.45 g of 2-tert-butyl-6-isothiocyanato-5-(4-methylpiperidin-1-yl)benzothiazole, described in Example 1, and 8.6 g of anhydrous piperazine in 30 ml of chloroform is stirred for 3 hours, washed with water, dried over anhydrous sodium sulphate and evaporated to get a sticky residue which is triturated with isopropanol and filtered to obtain 3 g of 2-tert-butyl-5-(4-methyl-piperidin-1-yl)-6-[(piperazin-1-yl)thiocarbonylamino]benzothiazole, melting at 278°-281°.

EXAMPLE 6

A solution of 2.0 g of 2-tert-butyl-6-isothiocyanato-5-(4-methylpiperidin-1-yl)benzothiazole and 0.78 g of 1-acetyl-piperazine in 30 ml of chloroform is stirred for 30 minutes and the product triturated with petroleum ether to obtain 6-[(4-acetyl-piperazin-1-yl)thiocarbonylamino]-2-tert-butyl-5-(4-methylpiperidin-1-yl)benzothiazole, melting at 187°-190°.

EXAMPLE 7

To a freshly prepared solution of sodium ethoxide (1.4 g of sodium in 100 ml of absolute ethanol) is added 5.2 g of 1-methyl-1-oxido-piperazine dihydrochloride. The mixture is stirred at 50° for 15 to 20 minutes and then at room temperature for 1 hour. The precipitated sodium chloride is filtered off and the filtrate is treated with a suspension of 8.6 g of 2-tert-butyl-6-isothiocyanato-5-(4-methylpiperidin-1-yl)benzothiazole, described in Example 1, in 25 ml of ethanol under stirring. The mixture is refluxed for 1 hour, cooled, concentrated under reduced pressure and the solid filtered to yield 3 g of 2-tert-butyl-5-(4-methyl-piperidin-1-yl)-6-(4-methyl-4-oxopiperazin-1-yl)thiocarbonylaminobenzothiazole, melting at 115°-117°.

EXAMPLE 8

A mixture of 69 g of 2-tert-butyl-6-isothiocyanato-5-(4-methylpiperidin-1-yl)benzothiazole and 39.2 g of N-acetyl-L-cysteine in 250 ml of dimethyl formamide is stirred under nitrogen atmosphere at room temperature for 72 hours, poured into water, the solid filtered and washed with water. The wet cake is dissolved in 500 ml of methylene chloride, dried over anhydrous sodium sulphate and treated with 1.5 l of hexane. The solid is filtered to give 85 g of S-(acetamido-2-carboxyethyl)-N-[2-tert-butyl-5-(4-methyl-piperidin-1-yl)benzothiazol-6-yl]dithiocarbamate, melting at 140°-143°.

EXAMPLE 9

Using the procedure described in Example 8, S-(acetamido-2-carboxyethyl)-N-[2-tert-butyl-5-(piperidin-1-yl)-6-benzothiazol-6-yl]dithiocarbamate, melting at 138°-140° can be prepared.

EXAMPLE 10

To a solution of 0.6 g of 6-amino-2-tert-butyl-5-(4-methylpiperidin-1-yl)benzothiazole and 0.36 g of 1-chloro-thiocarbonyl-4-methylpiperazine in 30 ml of dioxane is added 0.3 g of 1,8-diazabicyclo (5,4,0) undec-7-ene (DBU) and the mixture heated at 100° for 6 hours. The reaction mixture is evaporated to dryness, the residue triturated with water and the solid filtered. Chromatography of the solid over silica gel and elution with methylene dichloride-methanol (98:2) gives 2-tert-butyl-6-[(4-methyl-piperazin-1-yl)thiocarbonylamino]-5-(4-methylpiperidin-1-yl)benzothiazole, identical with the compound described in Example 1.

EXAMPLE 11

A solution of 0.5 g of 2-tert-butyl-5-(4-methyl-piperidin-1-yl)-6-phenoxythiocarbonylaminobenzothiazole and 0.11 g of 4-methylpiperazine in 20 ml of dioxane is refluxed for 16 hours. Evaporation of the solvent and chromatography of the residue over silica gel and elution with methylene dichloride-methanol (98:2) gives 2-tert-butyl-6-[(4-methylpiperazin-1-yl)thiocarbonylamino]-5-(4-methylpiperidin-1-yl)benzothiazole, identical with the compound described in Example 1.

The starting material for the above synthesis is prepared as follows:

A mixture of 1.5 g of 6-amino-2-tert-butyl-5-(4-methylpiperidin-1-yl)benzothiazole and 1.15 g of 0,0-diphenylthiocarbonate in 8 ml of pyridine is refluxed for 3.5 hours. The solvent is evaporated and the residue purified by chromatography over silica gel. Elution with methylene dichloride gives 2-tert-butyl-5-(4-methylpiperidin-1-yl)-6-phenoxythiocarbonylaminobenzothiazole melting at 201°-205°.

EXAMPLE 12

Compounds Tested

I. 2-Tert-butyl(6-[(4-methylpiperazin-1-yl)-thiocarbonylamino]-5-(4-methylpiperidin-1-yl)-benzothiazole (according to the invention)

II. 2-Tert-butyl-5-methyl-6-(N-methylpiperazinyl-thiocarbonylamino)-benzothiazole (according to U.S. Pat. No. 4,511,567 (Gallay et al.)

Methods and Results

Multimammate rats (*Mastomys natalensis*) of either sex and below 2-month-old were infected quantitatively with infective third stage larvae of any one of the four filariae: *Litomosoides carinni*, *Brugia pahangi*, *Brugia malayi* and *Dipetalonema viteae*. After the required prepatent period of each filarial species, the mastomys were checked for microfilariae by conventional blood smear examination. The positive animals were grouped randomly with 3-6 animals in each group.

The compounds, I and II were prepared in 0.2% carboxymethyl cellulose in distilled water and administered orally at different dosages and titrated successively through two-fold increase in dose. The effective doses of Compound I and the comparative test doses of Compound II are given in the Table.

The microfilarial counts in 10 μl of tail blood were monitored before and after treatment over the period of six weeks. The mastomys were sacrificed after six weeks and the search was made for adult worm recovery either live or dead from the respective sites of predilection.

The microfilaricidal and macrofilaricidal activity in the critical test design was calculated as per cent reduction in terms of pretreatment microfilarial counts and live and dead adult worms.

TABLE

Effect of Compound I and Compound II on four filariae an oral administration in *Mastomys natalensis*

| | Compound I | | | Compound II | | |
|---|---|---|---|---|---|---|
| Parasite | Dose (mg/kg/ days) | Percent Efficasy on MIF | MAF | Dose (mg/kg/ days) | Percent Efficasy on MIF | MAF |
| L. carinni | 37.5 × 1 | 99 | 99 | >25 × 5 | 0 | 0 |
| | | | | 50 × 5 | 0 | 0 |
| B. pahangi | 37.5 × 1 | 99 | 99 | >25 × 5 | 0 | 0 |
| | | | | 50 × 5 | 0 | 0 |
| B. malayi | 37.5 × 1 | 99 | 99 | >25 × 5 | 0 | 0 |
| | | | | 50 × 5 | 0 | 0 |

MIF = Microfilariae
MAF = Macrofilariae

Results summarised in the Table show that Compound I is effective against L. carinni, B. pahangi and B. malayi at a dose of 37.5 mg/kg/day (single dose) whereas Compound II is found to be inactive against both microfilariae and macrofilariae of all the above filatiae species in mastomys, at the tested dose range from >25 to 50 mg/kg/day for 5 days respectively. The results presented in the Table clearly demonstrate that Compound I is a potent microfilaricide as well as macrofilaricide, however Compound II does not exhibit any filaricidal activity in the respective species.

What is claimed is:

1. Benzazole derivatives of the formula I

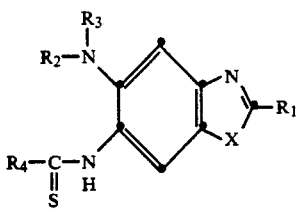

wherein X is oxygen or sulphur, $R_1$ is lower alkyl, lower alkenyl or cycloalkyl, $R_2$ and $R_3$ independently of one another are each hydrogen, lower alkyl or cycloalkyl radicals or taken together are a substituted or unsubstituted bivalent hydrocarbon residue of aliphatic character which contains between 4 and 7 carbon atoms in the chain and in which the 5-membered chain may be interrupted in its middle by oxygen, sulphur, or nitrogen, said nitrogen being optionally substituted by lower alkyl, phenyl, lower alkanoyl, benzoyl, lower alkoxycarbonyl or methanesulphonyl, $R_4$ is either a group

wherein $R_5$ and $R_6$ independently of one another are each hydrogen, lower alkyl or cycloalkyl radicals, optionally substituted, or taken together $R_5$ and $R_6$ are a substituted or unsubstituted bivalent hydrocarbon residue of aliphatic character which contains between 4 and 7 carbon atoms in the chain and in which the 5-membered chain may be interrupted in its middle by oxygen, sulphur, or nitrogen, said nitrogen being optionally substituted by lower alkyl, phenyl, lower alkanoyl, benzoyl, lower alkoxycarbonyl or methanesulphonyl, and their salts, and N-oxides.

2. A compound of formula I according to claim 1, wherein X is oxygen or sulphur, $R_1$ is lower alkyl, and $R_2$ and $R_3$ together represent a $C_4$–$C_7$-alkylene optionally interrupted in the middle position of the 5-membered chain by oxygen, sulphur or nitrogen wherein nitrogen is optionally substituted by lower alkyl, lower alkanoyl or lower alkoxycarbonyl group, and $R_4$ is a group

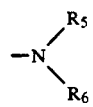

wherein $R_5$ and $R_6$ taken together are a $C_4$–$C_7$-alkylene optionally interrupted in the middle position of the 5-membered chain by oxygen or nitrogen optionally substituted by lower alkyl, lower alkanoyl or lower alkoxycarbonyl, and their salts and N-oxides.

3. A compound of formula I according to claim 1, wherein X is sulphur, $R_1$ is lower alkyl with 3 or 4 carbon atoms, $R_2$ and $R_3$ together represent a $C_4$–$C_7$-alkylene optionally interrupted in the middle position of the 5-membered chain by oxygen or nitrogen wherein nitrogen is optionally substituted by lower alkyl or lower alkoxycarbonyl, and $R_4$ is a group

wherein $R_5$ and $R_6$ together are a $C_4$–$C_7$-alkylene optionally interrupted in the middle position of the 5-membered chain by oxygen or nitrogen where nitrogen is optionally substituted by lower alkyl, lower alkanoyl or lower alkoxycarbonyl group, and their salts and N-oxides.

4. A compound of formula I according to claim 1, where X is sulphur, $R_1$ is tert-butyl, $R_2$ and $R_3$ together represent $C_5$alkylene optionally substituted by methyl, $R_4$ is a group

where $R_5$ and $R_6$ together represent $C_5$alkylene in which the middle carbon atom may be substituted by methyl or which may be interrupted in the middle of the alkylene chain by nitrogen, said nitrogen being optionally substituted by methyl, and their pharmaceutically acceptable salts and N-oxides.

5. A compound of formula I according to claim 1 being 2-Tert-butyl-6-[(morpholin-4-yl)thiocarbonylamino]-5-(piperidin-1-yl)benzothiazole and pharmaceutically acceptable salts thereof.

6. A compound of formula I according to claim 1 being L-$N^\delta$-[2-Tert-butyl-5-(piperidin-1-yl)benzothiazol-6-yl]-aminothiocarbonylarginine thereof.

7. A compound of formula I according to claim 1 being 2-Tert-butyl-5-(4-methyl-piperidin-1-yl)-6-[(piperazin-1-yl)thiocarbonylamino]benzothiazole or a pharmaceutically acceptable salt thereof.

8. A compound of formula I according to claim 1 being 6-[(4-Acetylpiperazin-1-yl)thiocarbonylamino]-2-tert-butyl-5-(4'-methylpiperazin-1-yl)benzothiazole or a pharmaceutically acceptable salt thereof.

9. A compound of formula I according to claim 1 being 2-Tert-butyl-5(4-methyl-piperidin-1-yl)-6-[(4-methylpiperazin-1-yl)thiocarbonylamino]benzothiazole or a pharmaceutically acceptable salt thereof.

10. A compound of formula I according to claim 1 being S-(Acetamido-2-carboxyethyl)-N-[2-tert-butyl-5-(4methyl-piperidin-1-yl)benzothiazol-6-yl]dithiocarbamate or a pharmaceutically acceptable salt thereof.

11. A compound of formula I according to claim 1 being S-(Acetamido-2-carboxyethyl)-N-[2tert-butyl-5-(piperidin-1-yl)-6benzothiazol-6yl]dithiocarbamate or a pharmaceutically acceptable salt thereof.

12. A pharmaceutical preparation comprising a compound of the formula I of claim 1.

13. A method for the treatment of lymphatic and tissue-dwelling filarial infections in an animal in need of such treatment which comprises the administration to said animal of an antifilarially effective amount of a compound according to claim 1 or a pharmaceutically acceptable salt thereof.

14. A method for the treatment of intestinal helminthic infections in an animal in need of such treatment which comprises the administration to said animal of an antihelminthically effective amount of a compound according to claim 1 or a pharmaceutically acceptable salt thereof.

15. A method for the treatment of lymphatic and tissue-dwelling filarial infections in an animal in need of such treatment which comprises the administration to said animal of an antifilarially effective amount of a benzazole derivative of the formula I

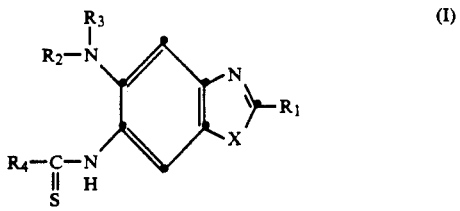

wherein X is sulphur, $R_1$ is lower alkyl, lower alkenyl or cycloalkyl, $R_2$ and $R_3$ independently of one another are each hydrogen, lower alkyl or cycloalkyl radicals or taken together are a substituted or unsubstituted bivalent hydrocarbon residue of aliphatic character which contains between 4 and 7 carbon atoms in the chain and in which the 5-membered chain may be interrupted in its middle by oxygen, sulphur, or nitrogen, said nitrogen being optionally substituted by lower alkyl, phenyl, lower alkanoyl, benzoyl, lower alkoxycarbonyl or methanesulphonyl, $R_4$ is either a group

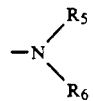

wherein $R_5$ and $R_6$ independently of one another are each hydrogen, lower alkyl or cycloalkyl radicals, optionally substituted, or taken together $R_5$ and $R_6$ are a substituted or unsubstituted bivalent hydrocarbon residue of aliphatic character which contains between 4 and 7 carbon atoms in the chain and in which the 5-membered chain may be interrupted in its middle by oxygen, sulphur, or nitrogen, said nitrogen being optionally substituted by lower alkyl, phenyl, lower alkanoyl, benzoyl, lower alkoxycarbonyl or methanesulphonyl, or of a pharmaceutically acceptable salt, or of an N-oxide thereof.

16. The method of claim 15, wherein X is sulphur, $R_1$ is lower alkyl, and $R_2$ $R_3$ together represent a $C_4$–$C_7$-alkylene optionally interrupted in the middle position of the 5-membered chain by oxygen, sulphur or nitrogen wherein nitrogen is optionally substituted by lower alkyl, lower alkanoyl or lower alkoxycarbonyl group, and $R_4$ is a group

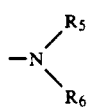

wherein $R_5$ and $R_6$ taken together are a $C_4$–$C_7$-alkylene optionally interrupted in the middle position of the 5-membered chain by oxygen or nitrogen optionally substituted by lower alkyl, lower alkanoyl or lower alkoxycarbonyl.

17. The method of claim 15, wherein X is sulphur, $R_1$ is lower alkyl with 3 or 4 carbon atoms, $R_2$ and $R_3$ together represent a $C_4$–$C_7$-alkylene optionally interrupted in the middle position of the 5-membered chain by oxygen or nitrogen wherein nitrogen is optionally substituted by lower alkyl or lower alkoxycarbonyl, and $R_4$ is a group

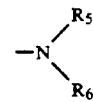

wherein $R_5$ and $R_6$ together are a $C_4$–$C_7$-alkylene optionally interrupted in the middle position of the 5-membered chain by oxygen or nitrogen where nitrogen is optionally substituted by lower alkyl, lower alkanoyl or lower alkoxycarbonyl group.

18. The method of claim 15, where X is sulphur, $R_1$ is tert-butyl, $R_2$ and $R_3$ together represent $C_5$alkylene optionally substituted by methyl, $R_4$ is a group

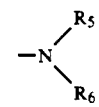

where $R_5$ and $R_6$ together represent $C_5$alkylene in which the middle carbon atom may be substituted by methyl or which may be interrupted in the middle of the alkylene chain by nitrogen, said nitrogen being optionally substituted by methyl.

19. The method of claim 15, wherein said derivative is 2-Tert-butyl-6-[(4-methyl-piperazin-1-yl)thiocarbonylamino]-5-(4-m ethylpiperidin-1-yl)benzothiazole or a pharmaceutically acceptable salt thereof.

20. A compound of formula I according to claim 1, wherein the compound is selected from the group consisting of 2-Tert-butyl-6-[(4-methylpiperazin-1-yl)thiocarbonylamino]-5-(4-methylpiperidin-1-yl)benzothiazole, 2-Tert-butyl-6-[(4-methyl-piperazin-1-yl)thiocarbonylamino]-5-(4-methylpiperazin-1-yl)benzothiazole, 2-Tert-butyl-6-[(piperidin-1-yl)-thiocarbonylamino]-5-(4-methylpiperazin-1-yl)benzothiazole, 2-Tert-butyl-5-[(piperidin-1-yl)-6-[(piperidin-1-yl)thiocarbonylamino]benzothiazole, 2-Tert-butyl-6-[(4-methylpiperazin-1-yl)thiocarbonylamino]-5-(piperidin-1-yl)benzothiazole, N-[2-Tert-butyl-5-(piperidin-1-yl)benzothiazol-6-yl]N'-(2-diethylaminoethyl)thiourea, N-[2-Tert-butyl-5-(piperidin-1-yl)benzothiazol-6-yl]-N'-[3-(piperidin-1-yl)propyl]thiourea, N-[2-Tert-butyl-5-(piperidin-1-yl)benzothiazol-6-yl]-N'-[3-(4-methylpiperazin-1-yl)propyl]thiourea, N-[2-Tert-butyl-5-(piperidin-1-yl)benzothiazol-6-yl]-N'-(3-(N.N-dimethylamino)propyl]thiourea, N-[2-Tert-butyl-5-(piperidin-1-yl)benzothiazol-6-yl]-N'-(2-hydroxyethyl)thiourea, and 2-Tert-butyl-6-[(4-methylpiperidin-1-yl)thiocarbonylamino]-5-(piperidin-1-yl)benzothiazole, or a pharmaceutically acceptable salt thereof.

* * * * *